United States Patent
Grant

(10) Patent No.: US 7,163,570 B2
(45) Date of Patent: *Jan. 16, 2007

(54) CHROMATOGRAPHIC METHOD OF SEPARATING RUTHENIUM FROM PLATINUM GROUP METALS

(75) Inventor: Richard Alasdair Grant, Reading (GB)

(73) Assignee: Anglo American Platinum Corporation Limited, Johannesburg (ZA)

(*) Notice: Subject to any disclaimer, the term of this patent is extended or adjusted under 35 U.S.C. 154(b) by 0 days.

This patent is subject to a terminal disclaimer.

(21) Appl. No.: 10/415,705

(22) PCT Filed: Oct. 26, 2001

(86) PCT No.: PCT/GB01/04745

§ 371 (c)(1),
(2), (4) Date: Dec. 22, 2003

(87) PCT Pub. No.: WO02/36837

PCT Pub. Date: May 10, 2002

(65) Prior Publication Data

US 2004/0079200 A1     Apr. 29, 2004

(30) Foreign Application Priority Data

Nov. 2, 2000   (GB) ................. 0026809.4

(51) Int. Cl.
*C22B 3/42* (2006.01)

(52) U.S. Cl. ...................................... 75/711

(58) Field of Classification Search ............... 75/722, 75/723, 744, 711, 101; 210/635, 656; 423/22, 423/DIG. 14

See application file for complete search history.

(56) References Cited

U.S. PATENT DOCUMENTS

| 4,105,442 A | 8/1978 | Fieberg et al. |
| 4,130,625 A * | 12/1978 | Evers et al. .................. 423/22 |
| 4,885,143 A | 12/1989 | Schmuckler |
| 5,478,376 A | 12/1995 | Grant et al. |
| 6,365,049 B1 * | 4/2002 | Smith ........................ 210/635 |

FOREIGN PATENT DOCUMENTS

| EP | 0 756 013 A1 | 1/1997 |
| EP | 0 906 962 A1 | 4/1999 |
| EP | 1 074 635 A1 | 2/2001 |

(Continued)

OTHER PUBLICATIONS

Frank Bottomley, "Nitrosyl Complexes of Ruthenium," *Coordination Chemistry Reviews*, vol. 26, No. 1, Jun. 1978, pp. 7-32.

(Continued)

*Primary Examiner*—Roy King
*Assistant Examiner*—Kathleen Mcnelis
(74) *Attorney, Agent, or Firm*—RatnerPrestia

(57) ABSTRACT

A chromatographic separation method separates ruthenium from other platinum group metals in a feed solution, by converting the Ru to a nitrosyl complex, retaining the nitrosyl complex temporarily on the chromatography column and subsequently eluting Ru, for example using an oxidising or reducing eluent. FIG. 1 shows the elution profile obtained from a mixture of Rh chloro-complexes (Peak 1) and Ru nitrosyl species (Peak 2).

13 Claims, 3 Drawing Sheets

FOREIGN PATENT DOCUMENTS

GB          2 293 372 A          3/1996

OTHER PUBLICATIONS

E. E. Mercer, W. M. Campbell, Jr., and R. M. Wallace, "Chloro Complexes of Nitrosylruthenium," *Inorganic Chemistry,* vol. 3, No. 7, 1964, pp. 1018-1024.

Michael J. Hudson, Kevin D. Helps, and Alan Dyer, "Selective Extraction of Ruthenium-Nitrosyl Cations Using Modified Inorganic Materials," (Cambridge: Royal Society of Chemistry, 1993, Special Publication No. 122), pp. 289-297.

International Search Report from International Appl. No. PCT/GB01/04745, dated Jan. 31, 2002.

British Search Report from British Application No. 0026809.4 dated May 24, 2001.

* cited by examiner

CHROMATOGRAPHIC METHOD OF SEPARATING RUTHENIUM FROM PLATINUM GROUP METALS

This application is the U.S. national phase application of PCT International Application No. PCT/GB01/04745.

FIELD OF THE INVENTION

The present invention relates to methods for the interseparation of platinum group metals, in particular it relates to methods for the interseparation of one or more of platinum, palladium, ruthenium, rhodium, iridium and osmium.

BACKGROUND OF THE INVENTION

Previously, it has been proposed to use gel chromatography to separate platinum group metals (PGMs) from one another on an industrial scale. Prior proposals include U.S. Pat. No. 4,885,143 (Schmuckler). This patent describes a method in which the interseparation of platinum group metals (PGMs) from an oxidised gold-free halide solution is achieved using a chromatographic medium such as a polysaccharide gel (Sephadex) or a polyacrylamide gel (Biogel). The PGMs when dissolved in a chloride solution are absorbed onto the chromatographic column and are claimed to be selectively eluted in the order ruthenium, rhodium, palladium, platinum, iridium and caesium, although it is clear from the rest of the patent that Schmuckler meant osmium rather than caesium. The problem with this method is that there is in fact no clear separation of PGMs.

This problem was to a large extent overcome by European patent application EP 756013 (Matthey Rustenburg Refiners Pty) which describes a method for the interseparation of PGMs from a PGM-containing halide solution comprising the steps of passing the solution through a glycol methacrylate chromatographic medium, absorbing the PGMs onto the medium, eluting each PGM using an acid solution to obtain each fraction containing at least one PGM. During the elution of a reduced, mixed rhodium, iridium, ruthenium, palladium, platinum and osmium/6 molar hydrochloric acid (6 M HCl) solution through Toyopearl HW-40C using a (usually 6 M) hydrochloric acid eluent, the first eluted band contains trivalent rhodium iridium and ruthenium (which will be subsequently referred to as rhodium (III), iridium (III) and ruthenium (III)), that is, the method does not separate rhodium, iridium and ruthenium either from each other or any combinations/permutations within.

The present invention sets out to address the problem of the separation of the metals rhodium, iridium and ruthenium, from one another in addition to other PGMs using gel chromatography. This may be of particular importance, allowing the separation of these metals by chromatography on an industrial scale. Presently, refining processes involve solvent extraction, distillation and ion exchange. The metals are processed sequentially, for example in the order osmium, gold, palladium, platinum, ruthenium, iridium and rhodium. The method of the present invention has several advantages over the previously described methods in allowing simultaneous separation of some or all of these metals. In addition, the process is extremely fast, and the purity and yield of the extracted metals is high.

Ruthenium is unique amongst the platinum group metals in that it forms extremely stable nitrosyl complexes (containing the $NO^+$ moiety) and indeed has a well documented nitrosyl literature (Coord.Chem.rev (1978) 26 (1), 7–32, Mercer et al. Inorganic Chemistry, Vol 3 No7, 1964 pg 1018). An extensive study has been previously performed by the present inventors looking at the potential use of ruthenium nitrosyl species in precious metal refining. Of relevance in the present context is that in 6 M HCl, there are two major ruthenium nitrosyl species present: $[Ru(NO)Cl_5]^{2-}$ and $[Ru(NO)Cl_4(H_2O)]^-$. In both complexes, the ruthenium is formally present in its divalent oxidation state. The $[Ru(NO)Cl_5]^{2-}$ and $[Ru(NO)Cl_4(H_2O)]^-$ species are in equilibrium, the equilibrium ratio at 6 M chloride concentration being approximately 2:1. As the chloride concentration decreases, the relative amount of the $[Ru(NO)Cl_4(H_2O)]^-$ species increases and as the chloride concentration increases, the relative amount of the $[Ru(NO)Cl_5]^{2-}$ species increases.

There are a number of literature methods (GB 2293372, Matthey Rustenburg Refiners PTY, Spec Publ. -Roy Soc. Chem (1993), 122) for preparing ruthenium nitrosyl species including the use of sodium nitrite, nitric oxide gas and nitric acid with a reductant. The method used to date has involved the use of formic (HCOOH) and nitric ($HNO_3$) acids.

SUMMARY OF THE INVENTION

The present inventors have found that when a 6 M HCl solution containing the $[Ru(NO)Cl_5]^{2-}/[Ru(NO)Cl_4(H_2O)]^-$ species is eluted through either Toyopearl HW-40C resin or Sephadex G-10 resin, the $[Ru(NO)Cl_5]^{2-}$ elutes quicker than the $[Ru(NO)Cl_4(H_2O)]^-$ thus affording a substantial resolution of the two species in the final chromatogram. In addition both species have differing retention times to the trivalentchloro complexes of Rh, Ir and Ru. Thus, the conversion of ruthenium into nitrosyl species combined with the use of gel chromatography may be an industrially useful method of the separation of PGMs.

Thus in a first aspect the present invention provides a method for the interseparation of ruthenium in admixture with one or more other PGMs from a feed solution containing complexes of these metals by passing said solution through at least one chromatography column containing an absorbant and eluting one or more fractions containing one or more PGMs which comprises the steps of:
  (a) ensuring that ruthenium is present on the column as at least one of the following species: $[Ru(NO)Cl_5]^{2-}$ and $[Ru(NO)Cl_4(H_2O)]^-$ and,
  (b) applying at least one eluent to at least one column thereby effecting the elution of ruthenium separately from the complexes of other PGMs present.

In one embodiment of the invention, the eluent may comprise an oxidising agent. This may be used in order to prevent the reduction of small amounts of iridum (IV) to iridium (III) on the column. Suitable oxidising eluents include but are not limited to 1M HCl/5 $gl^{-1}NaClO_3$ and hydrogen peroxide. In an alternative embodiment, the in situ reduction of tetravalent iridium to trivalent iridum may be performed using a reducing eluent after elution of the nitrosyl species using an oxidising eluent. Suitable reducing eluents include but are not limited to 1MHCl/ascorbic acid and $TiCl_3$. This may improve the separation of the PGMs further. The term in situ reduction in the context of the present invention means reduction on the column. Using these techniques palladium will not be substantially separated from the Ru-nitrosyl species.

The inventors have found that the conversion of ruthenium into nitrosyl species combined with the in situ reduction of tetravalent iridium to trivalent iridium and the use of reverse elution can be used to improve the separation of the PGMs further still. Reverse elution in the context of this invention means that the direction of eluent flow (and the subsequent elution of any one or more PGMs) is reversed. For example, in the present invention the direction of eluent flow is changed from downwards to upwards.

Thus in a second aspect, the present invention provides a method for the interseparation of ruthenium in admixture with one or more other PGMs from a feed solution containing complexes of these metals by passing said solution through at least one chromatography column containing an absorbant and eluting one or more fraction containing one or more PGMs which comprises the steps of:
  (a) ensuring that ruthenium is present on the column as at least one of the following species: $[Ru(NO)Cl_5]^{2-}$ and $[Ru(NO)Cl_4(H_2O)]^-$ and,
  (b) using at least one oxidising eluent to effect the elution of at least one ruthenium nitrosyl species from the column, whilst maintaining the iridium in the tetravalent oxidation state, and
  (c) using at least one reducing eluent on at least one column to reduce the iridum from a tetravalent oxidation state to a trivalent oxidation state and improving the separation of the complexes of PGMs by reverse elution.

The chromatographic medium is preferably a co-polymer of oligoethyleneglycol, glycidylmethacrylate pentaerythroldiethacrylate (for example a medium from the Toyopearl (trademark of TosoHaas and previously known as Fractogel) range of chromatographic media). This medium has advantages in the scaling up of the chromatographic process because high pressure can be applied to a column containing the medium to achieve high flow rates. Alternatively or in addition the medium may be a co-polymer of ethylene glycol and methacrylic acid, for example a medium from the Macro Prep (trademark of Bio-Rad Laboratories) range of chromatographic media Other suitable chromatographic media include but are not limited to Sephadex (cross-linked dextran and epichlorohydrin).

The PGMs are preferably dissolved in an acidic solution such as hydrochloric acid. Preferably, the oxidising eluent is 1M HCl/5 gl$^{-1}$ NaClO$_3$. Other oxidising eluents may include acidified hydrogen peroxide. Preferably, the reducing eluent is 1M HCl/ascorbic acid. The concentration of ascorbic acid may be anywhere between 2 and 15 gl$^{-1}$. In a preferred embodiment, the concentration of ascorbic acid is 9 gl$^{-1}$. Other suitable reducing eluents may include TiCl$_3$.

The interseparation process may be carried out using a chromatographic medium having beads of any particle size. However, suitably, the medium has beads of mean particle size of from 30 to 180 um, and preferably of from 40 to 100 um.

The interseparation may be carried out using known chromatographic techniques. A suitable chromatographic method is batch column chromatography whereby an aliquot of feed is loaded onto the column and eluted. A valve arrangement is employed such that the output can be switched so that various products are collected in separate fractions. An alternative suitable method is continuous annular chromatography. These methods will be known to those skilled in the art.

DETAILED DESCRIPTION OF THE INVENTION

The invention will now be described with reference to the figures and to the following examples which are in no way limiting.

Figure 1:
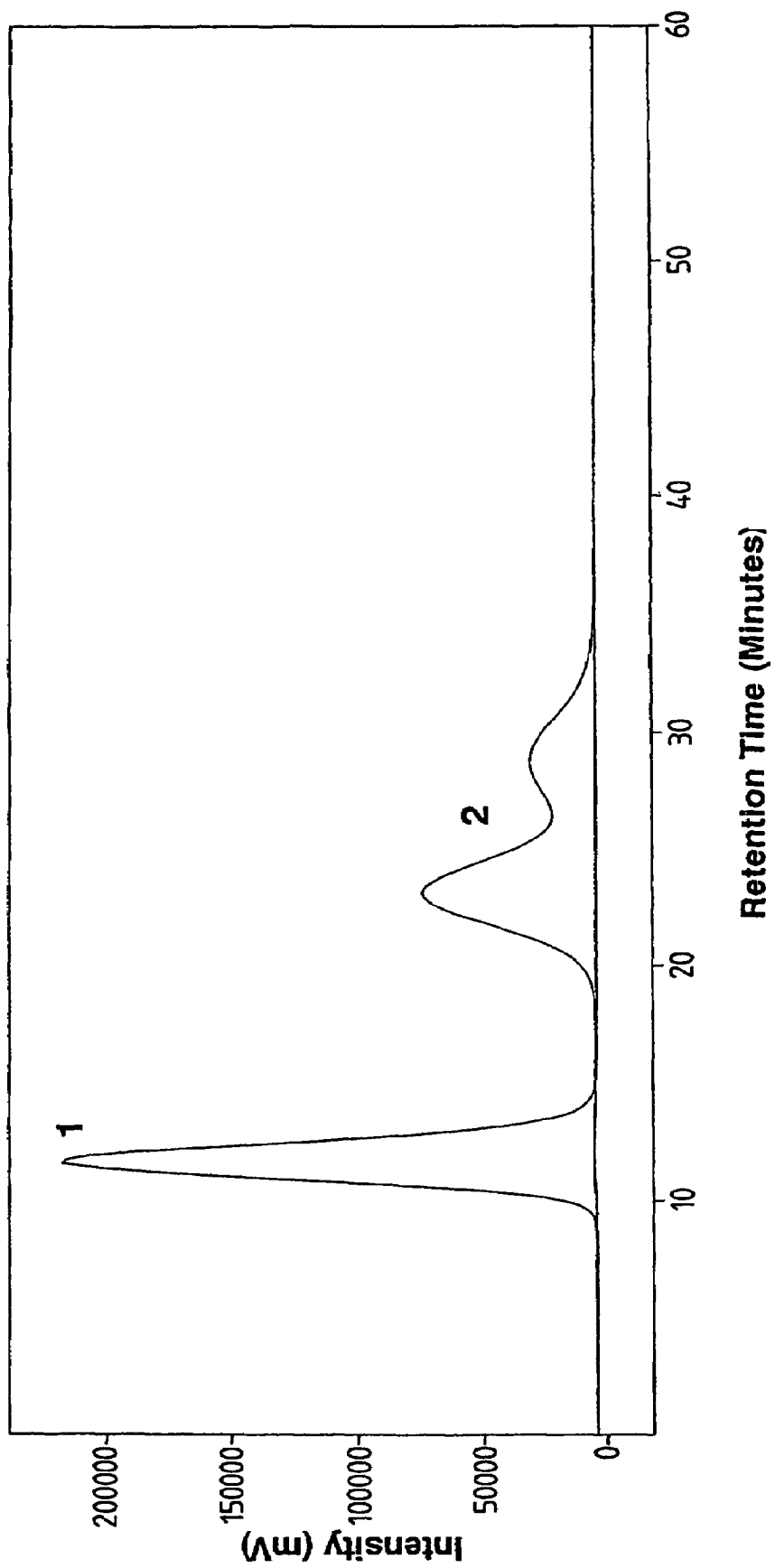
FIG. 1 is a an elution plot of intensity over retention time for a solution containing Rh (III) chioro complexes and Ru-nitrosyl species.

FIG. 1: shows the separation profile obtained when a 6 M HCl solution containing Rh (III) chloro complexes and Ru-nitrosyl species are eluted through Toyopearl HW-40C using a 6 M HCl eluent. Horizontal axis represents time in minutes and the vertical axis represents intensity in millivolts (mV) measured using inductively coupled plasma emission (ICP) spectroscopy. It is a measure of the relative metal concentration at that point in time. Peak 1 represents the trivalent Rh-chlorocomplexes, peak 2 represents Ru Nitrosyl species $[Ru(NO)Cl_5]^{2-}$-$[Ru(NO)Cl_4(H_2O)]^-$ respectively.

Figure 2:
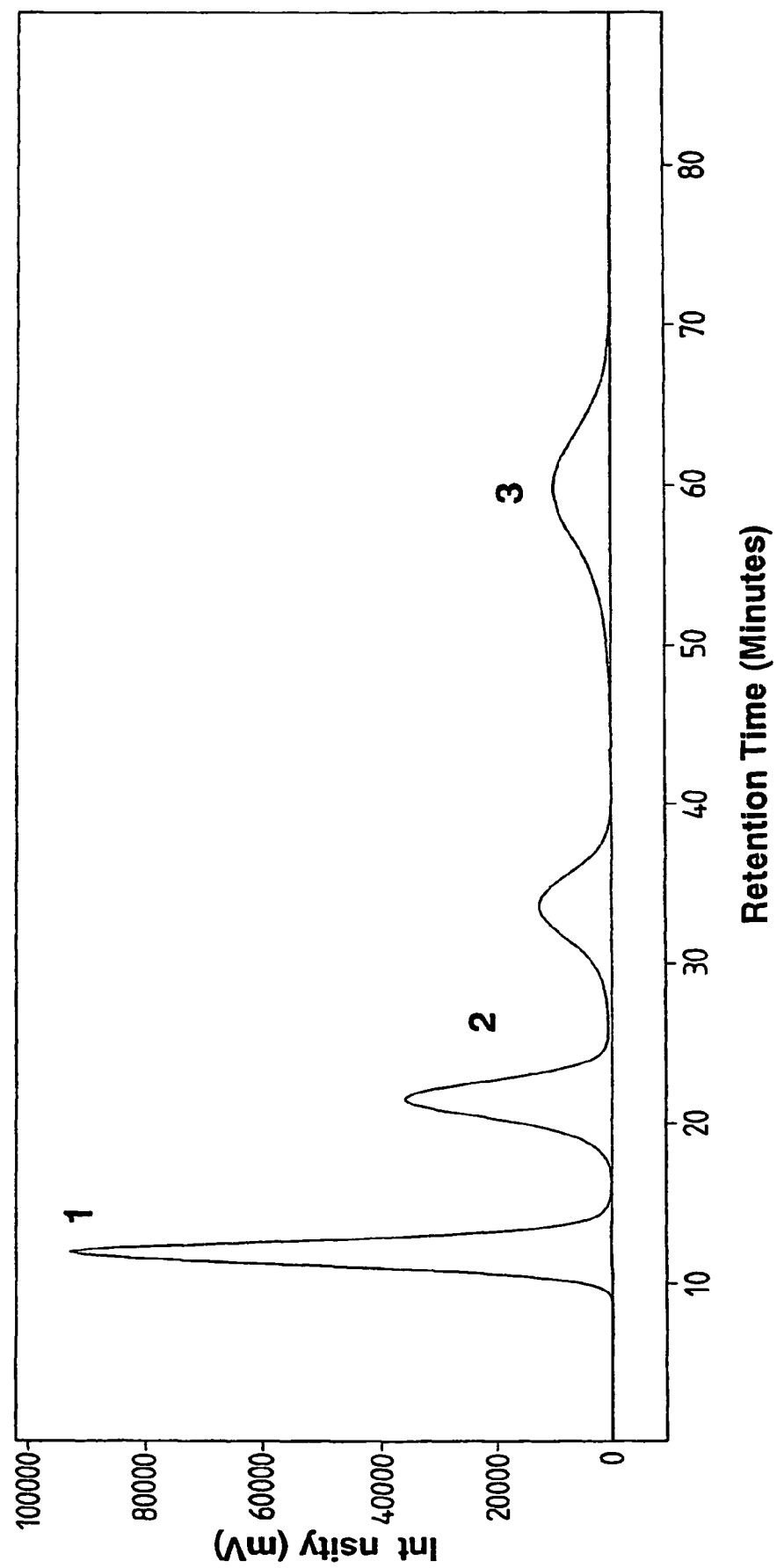
FIG. 2 is a an elution plot of intensity over retention time for a solution containing trivalent rhodium, ruthenium nitrosyl species and tetravalent iridium chlorocomplexes.

FIG. 2: shows the separation of trivalent rhodium, ruthenium nitrosyl species and tetravalent iridium chlorocomplexes through Toyopearl HW-40C using an oxidising eluent Horizontal axis represents time in minutes and the vertical axis represents intensity in millivolts (mV) measured using ICP spectroscopy. It is a measure of the relative metal concentration at that time. Peak 1 represents trivalent Rh-chlorocomplexes, peak 2 represents Ru-nitrosyl species $[Ru(NO)Cl_5]^{2-}$ and $[Ru(NO)Cl_4H_2O)]^-$ respectively, and peak 3 represents tetravalent Iridium chlorocomplexes.

Figure 3:
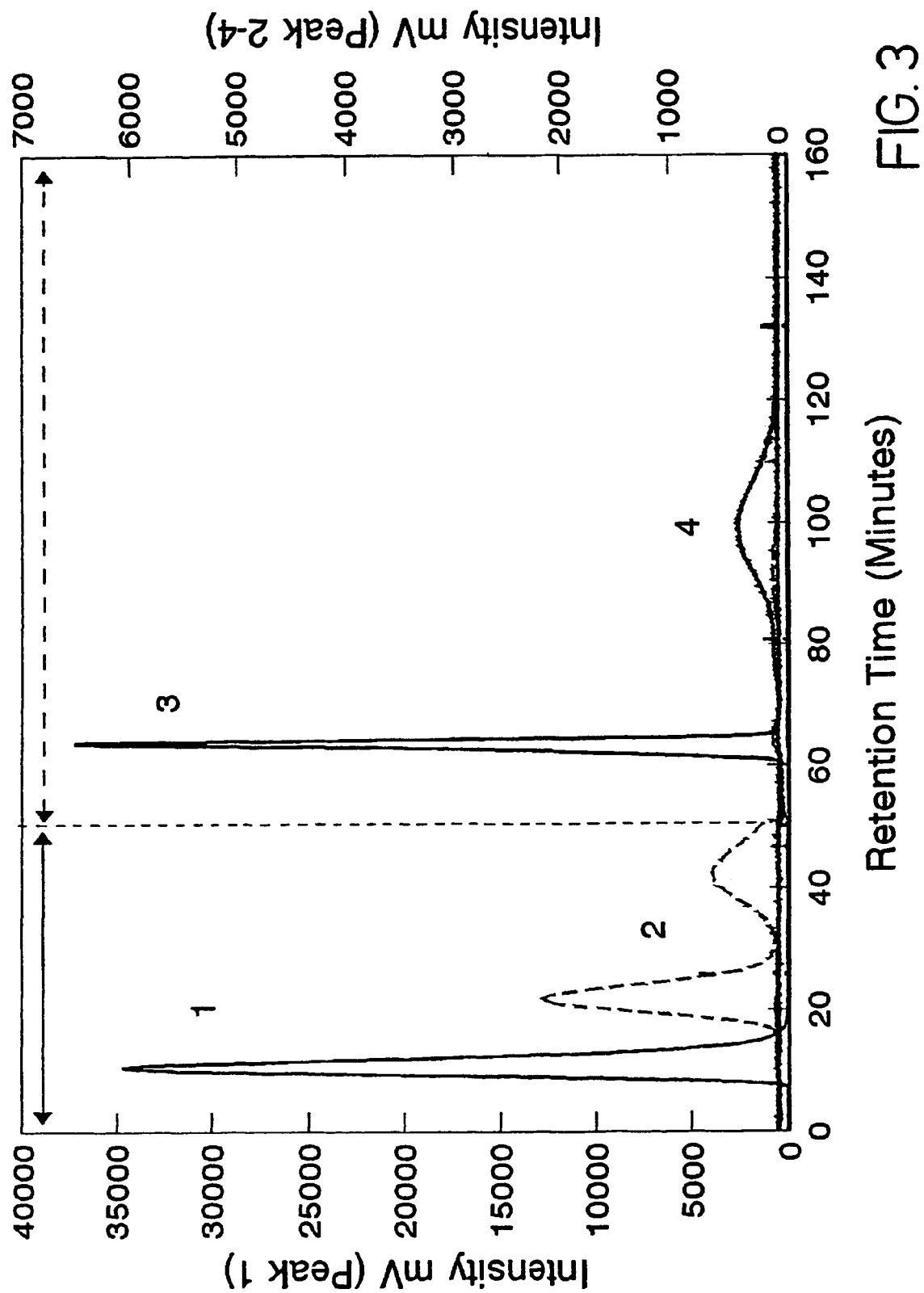
FIG. 3 is a an elution plot of intensity over retention time for a solution containing trivalent rhodium, ruthenium nitrosyl species, iridium (IV) to iridium (III) and tetravalent platinum using forward/reverse and oxidizing/reducing elements.

FIG. 3: shows the separation of trivalent rhodium, ruthenium nitrosyl species, iridium (IV) to iridium (III) and tetravalent platinum using forward/reverse elution and oxidising/reducing eluents. Separation was carried out using a Sephadex G-10 column. Horizontal axis represents time in minutes and the vertical axis represents millivolts measured using ICP spectroscopy. It is a measure of the relative metal concentration at that point in time. Peak 1 represents trivalent Rh$^-$ chlorocomplexes, peak 2 represents Ru-nitrosyl species $[Ru(NO)Cl_5]^{2-}$ and $[Ru(NO)Cl_4(H_2O)]^-$ respectively, peak 3 represents the peak arising from the in situ reduction of tetravalent to trivalent iridium, peak 4 represents tetravalent Pt-chlorocomplexes, predominantly $[PtCl_6]^-$. Straight line arrows represent 'downwards' elution with 1M HCl/5 gl$^{-1}$ NaClO$_3$. Dashed arrows represent 'upwards' elution with 1M HCl/9 gl$^{-1}$ ascorbic acid.

EXAMPLE 1

FIG. 1 shows the separation profile obtained when a 6 M HCl solution containing rhodium (III) chlorocomplexes and $[Ru(NO)Cl_5]^{2-}$/$[Ru(NO)Cl_4(H_2O)]^-$ is eluted through Toyopearl HW-40C. A separation of the rhodium and ruthenium is clearly apparent. The complexes were applied to the column in a 6M HCl feed solution. the eluent was 6M HCl. A flow rate of 1.5 ml/min was used and the method of batch column chromatography employed.

EXAMPLE 2

Iridium ($[IrCl_6]^{2-}$) can be added to the rhodium (III)/[Ru(NO)Cl$_5$]$^{2-}$/[Ru(NO)Cl$_4$(H$_2$O)]$^-$/6 M HCl solution and a separation of rhodium, ruthenium and iridium is achieved if an oxidising eluent is used. This is shown in FIG. 2. A 1M HCl/5 gl$^{-1}$ NaClO$_3$ eluent is used. The column employed was a Toyopearl HW-40C, 300 mm×10 mm. The flow rate used was 1.5 ml/min and the method of batch column chromatography used.

EXAMPLE 3

A separation of the rhodium, ruthenium, platinum and iridium can be achieved by utilising the in-situ reduction of iridium (IV) to iridium (III). The resolution between the metals can be further improved by employing the forward/reverse elution technique. The separation is effected as follows: The 6M HCl feed solution containing rhodium (III), Pt (IV) and Ir (IV) and Ru nitrosyl complexes is loaded onto the top of the column (Sephadex G10) and eluted with an oxidising eluent (1 M HCl/5 gl$^{-1}$ NaClO$_3$) until the [Ru(NO)Cl$_4$(H$_2$O)]— species has eluted. At this point, the eluent is changed from oxidising to reducing (1 M HCl/9 gl$^{-1}$ ascorbic acid) and the direction of the elution changed from downwards to upwards ie is reversed. The $[IrCl_6]^{2-}$ is then reduced on the column and the resulting iridium (III) is eluted upwards along with the $[PtCl_6]^{2-}$. The resulting elution profile showing the separation of the Rh (III), [Ru(NO)Cl$_5$]$^{2-}$/[Ru(NO)Cl$_4$(H$_2$O)]$^-$, Ir (IV) reduced to Ir(III) and $[PtCl_6]^{2-}$ is shown in FIG. 3. It is apparent that a combination of the ruthenium nitrosyl, in-situ Ir (IV) to Ir (III) reduction and forward/reverse elution techniques have been used to achieve a separation of the rhodium, ruthenium, iridium and platinum.

The invention claimed is:

1. A method for the interseparation of ruthenium, rhodium and iridium metals from a feed solution containing chlorocomplexes of these metals, the method comprising passing said solution through at least one chromatography column containing an absorbent, and the steps of:
   (a) ensuring that ruthenium is present on the column as at least one of the following species: [Ru(NO)Cl$_5$]$^{2-}$ and [Ru(NO)Cl$_4$(H$_2$O)]$^-$;
   (b) ensuring that iridium is present on the column as a tetravalent species; and,
   (c) applying an oxidizing eluent to the at least one column thereby effecting the elution of the metal chlorocomplexes, separately from one another and in the order rhodium, ruthenium, iridium.

2. A method for the interseparation of a ruthenium metal in admixture with one or more other PGM metals, including iridium, from a feed solution containing chlorocomplexes of these metals by passing said solution through at least one chromotagraphy column containing an absorbent and eluting one or more fraction containing one or more PGMs, which comprises the steps of:
   (a) ensuring that ruthenium is present on the column as at least one of the following species: [Ru(NO)Cl$_5$]$^{2-}$ and [Ru(NO)Cl$_4$(H$_2$O)]$^-$;
   (b) using at least one oxidizing eluent to effect the elution of at least one ruthenium nitrosyl species from the column, while maintaining iridium in a tetravalent oxidative state; and,
   (c) using at least one reducing eluent on the at least one column to reduce the iridium from a tetravalent oxidation state to a trivalent oxidation state and improving the separation of the chiorocomplexes of PGMs by reverse elution.

3. A method according to claim 1, wherein the oxidizing eluent is IMHCl/5 gl$^{-1}$ NaClO$_3$ or hydrogen peroxide.

4. A method according to claim 2, wherein the reducing eluent is 1MHCl/9 gl$^{-1}$ ascorbic acid.

5. A method according to claim 1, wherein the feed solution includes hydrochloric acid.

6. A method according to claim 1, wherein the absorbent is selected from the group consisting of at least one of:
   a copolymer of ethylene glycol and methacrylic acid,
   a copolymer of oligoethyleneglycol glycidylmethacrylate pentaerythrol-dimethacrylate,
   cross-linked dextran and epichlorohydrin.

7. A method according to claim 1, wherein the absorbent is in bead form with a particle size of from 40–100 μm.

8. A method according to claim 2, wherein the oxidizing eluent is IMHCl/5 gl$^{-1}$ NaClO$_3$ or hydrogen peroxide.

9. A method according to claim 2, wherein the feed solution includes hydrochloric acid.

10. A method according to claim 2, wherein the absorbent is selected from the group consisting of at least one of:
    a copolymer of ethylene glycol and methacrylic acid,
    a copolymer of oligoethyleneglycol glycidylmethacrylate pentaerythrol-dimethacrylate,
    cross-linked dextran and epichiorohydrin.

11. A method according to claim 2, wherein the absorbent is in bead form with a particle size of from 40–100 μm.

12. A column chromatography method for separating at least one of the following ruthenium nitrosyl species: [Ru(NO)Cl$_5$]$^{2-}$ and [Ru(NO)Cl$_4$(H$_2$O)]$^-$, from a feed solution comprising at least one ruthenium nitrosyl species, a tetravalent iridium species, and a rhodium chlorocomplex, the method comprising the steps of:
    providing a feed solution comprising the at least one ruthenium nitrosyl species, the tetravalent iridium species, and the rhodium chlorocomplex;
    absorbing the at least one ruthenium nitrosyl species, the tetravalent iridium species, and the rhodium chlorocomplex on a chromatography column;
    providing an eluant comprising an oxidizing agent;
    eluting the at least one ruthenium nitrosyl species off the chromatography column after the rhodium chiorocomplex with the oxidizing eluant to separate the at least one ruthenium nitrosyl species from the remainder of the feed solution.

13. The method according to claim 12 after the at least one ruthenium nitrosyl species is separated from the remainder of the feed solution, the method further comprises:
    providing an eluant comprising a reducing agent; and
    eluting the tetravalent iridium species off the chromatography column with the reducing eluant by reducing the tetravalent iridium to trivalent iridium.

* * * * *

UNITED STATES PATENT AND TRADEMARK OFFICE
CERTIFICATE OF CORRECTION

PATENT NO.         : 7,163,570 B2
APPLICATION NO. : 10/415705
DATED               : January 16, 2007
INVENTOR(S)      : Richard Alasdair Grant Page 1 of 1

It is certified that error appears in the above-identified patent and that said Letters Patent is hereby corrected as shown below:

At column 6, line 4, delete "chiorocomplexes" and insert --chlorocomplexes--.

At column 6, line 33, delete "epichiorohydrin" and insert --epichlorohydrin--.

At column 6, lines 52-53, delete "chiorocomplex" and insert --chlorocomplex--.

Signed and Sealed this

Twenty-seventh Day of May, 2008

JON W. DUDAS
*Director of the United States Patent and Trademark Office*